United States Patent [19]
Oyola

[11] Patent Number: 6,162,255
[45] Date of Patent: Dec. 19, 2000

[54] STEM OFFSET MECHANISM FOR JOINT PROSTHESIS

[75] Inventor: Arnold E. Oyola, Taunton, Mass.

[73] Assignee: DePuy Orthopaedics, Inc., Warsaw, Ind.

[21] Appl. No.: 09/173,139

[22] Filed: Oct. 15, 1998

[51] Int. Cl.[7] .................................................. A61F 2/38
[52] U.S. Cl. ...................... 623/20.34; 623/20.15
[58] Field of Search ........................ 623/18, 20, 23, 623/20.14, 20.15, 20.34

[56] References Cited

U.S. PATENT DOCUMENTS

| | | | |
|---|---|---|---|
| 4,538,305 | 9/1985 | Engelbrecht et al. | 623/20 |
| 4,822,366 | 4/1989 | Bolesky | 623/20 |
| 4,904,110 | 2/1990 | Klein | 403/379 |
| 4,936,853 | 6/1990 | Fabian et al. | 623/20 |
| 4,950,297 | 8/1990 | Elloy et al. | 623/20 |
| 4,985,037 | 1/1991 | Petersen | 623/20 |
| 5,002,581 | 3/1991 | Paxson et al. | 623/18 |
| 5,127,914 | 7/1992 | Calderale et al. | 606/65 |
| 5,133,760 | 7/1992 | Petersen et al. | 623/20 |
| 5,152,796 | 10/1992 | Slamin | 623/20 |
| 5,194,066 | 3/1993 | Van Zile | 623/20 |
| 5,226,915 | 7/1993 | Bertin | 623/20 |
| 5,271,737 | 12/1993 | Baldwin et al. | 623/20 |
| 5,290,313 | 3/1994 | Heldreth | 623/20 |
| 5,326,359 | 7/1994 | Oudard | 623/20 |
| 5,330,534 | 7/1994 | Herrington et al. | 623/20 |
| 5,336,225 | 8/1994 | Zang | 606/73 |
| 5,507,824 | 4/1996 | Lennox | 623/22 |
| 5,545,228 | 8/1996 | Kambin | 623/17 |
| 5,556,433 | 9/1996 | Gabriel et al. | 623/20 |
| 5,683,472 | 11/1997 | O'Neil et al. | 623/20 |
| 5,776,200 | 7/1998 | Johnson et al. | 623/20 |
| 5,782,920 | 7/1998 | Colleran | 623/20 |
| 5,782,921 | 7/1998 | Colleran et al. | 623/20 |
| 5,944,756 | 8/1999 | Fischetti et al. | 623/18 |

FOREIGN PATENT DOCUMENTS

| | | | |
|---|---|---|---|
| 529408 | 3/1993 | European Pat. Off. | A61F 2/38 |
| 473375 | 3/1929 | Germany. | |

OTHER PUBLICATIONS

Johnson & Johnson Orthopaedics Research & Development, "P.F.C.® Modular Knee System Research Data and Laboratory Testing", cover and pp. 8, 36, & 37 (1989).

*Primary Examiner*—Bruce Snow
*Attorney, Agent, or Firm*—Nutter, McClennen & Fish, LLP

[57] ABSTRACT

A joint prosthesis system allows an inferior component of a prosthesis system to be offset from a superior component of the system. In one embodiment the joint prothesis comprises a tibial tray having an offset tibial stem. A bolt member connects between the tibial tray and tibial stem to provide the desired degree of offset and the orientation of the offset. The bolt member is constructed such that a longitudinal axis extending through a first end thereof is offset from a longitudinal axis extending through a second end thereof.

11 Claims, 6 Drawing Sheets

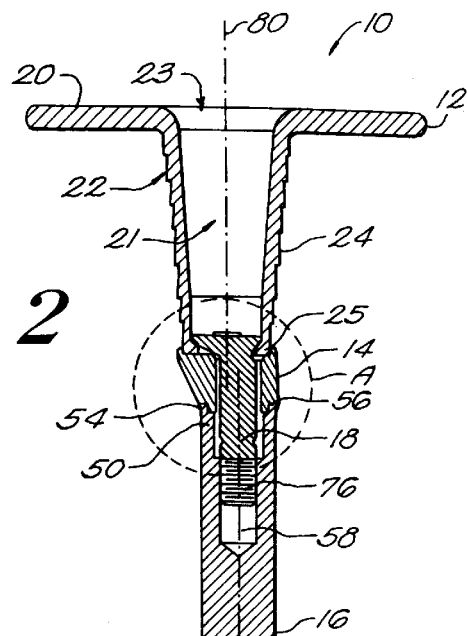
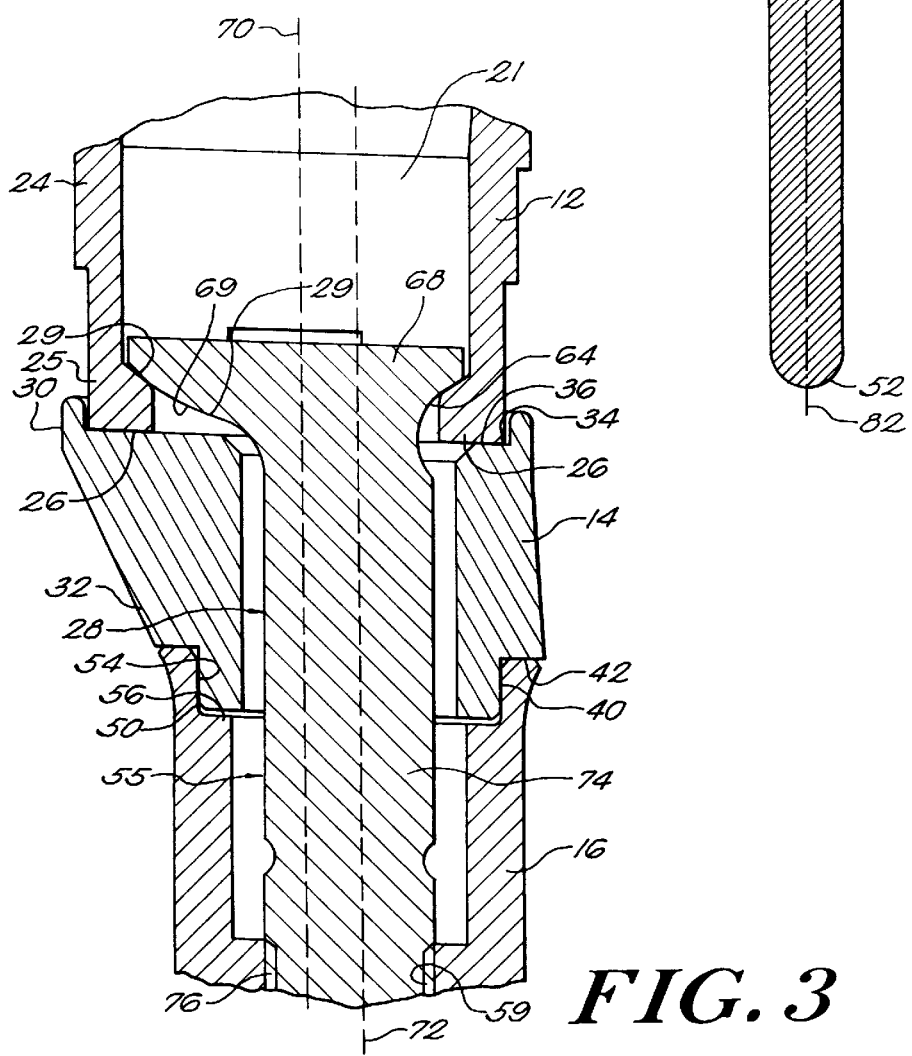
FIG. 2
FIG. 3

STEM OFFSET MECHANISM FOR JOINT PROSTHESIS

CROSS-REFERENCE TO RELATED APPLICATIONS

Not applicable.

STATEMENT REGARDING FEDERALLY SPONSORED RESEARCH

Not applicable.

FIELD OF THE INVENTION

The invention relates to modular joint prothesis components. More particularly, the invention relates to knee prosthesis components in which the tibial stem is offset with respect to a longitudinal axis of the tibial tray.

BACKGROUND OF THE INVENTION

Various joint prosthesis components include elongate stems that are to be mounted within the intramedullary canal of a bone while the other end is attached to another prosthesis component that is mounted upon the bone. Such stems are used, for example, with femoral knee stems and tibial knee stems.

Knee arthroplasty procedures involve the installation of a femoral component on the patient's femur and a tibial component on the patient's tibia. The tibial component usually comprises a tibial stem which is attachable to a tibial tray. The tibial stem is designed to be installed within the intramedullary canal of the tibia while the tibial tray mounts upon a prepared surface on the head of the tibia. A tibial bearing member, which articulates with the femoral component, is typically mounted upon the tibial tray.

The variations in the human anatomy of different patients, especially in bones such as the tibia, creates the need for a variety of implant sizes and configurations. In some instances, it is necessary that the longitudinal axis of a stem component, such as a tibial stem, be laterally offset from the longitudinal axis of the other prosthesis component, such as the tibial tray. In many individuals however, these axes must be offset with respect to one another to ensure proper implantation. Even where offset is required, there is no uniformity as to the degree or direction of offset.

Modular prosthesis systems have been developed to accommodate the variability in patient anatomies. Modular systems include a number of interchangeable parts, each having different sizes or other physical characteristics. Such modular systems are useful in that they allow surgeons to use one or more standard parts with interchangeable components having different characteristics.

U.S. Pat. No. 5,290,313 discloses a modular tibial prothesis in which a tibial stem is mounted so as to be laterally offset with respect to the longitudinal axis of a tibial tray. A coupling allows specially designed tibial stems to be mounted to the tibial tray to achieve a desired offset orientation. One disadvantage of this design is that the tibial stems themselves are offset, and a different stem must be used to achieve a desired offset orientation. As a result, a number of different, non-standard tibial stems are needed to achieve the desired offset orientation required for a given patient. Such a system can increase the cost of prostheses because several non-standard parts are necessary to cope with all possible anatomical requirements of patients.

Thus it would be desirable to have a modular prosthesis system which could accommodate the variability in patient anatomies and allow greater flexibility to the surgeon, while still providing the ability for the tibial bearing insert to rotate with respect to the tibial tray.

SUMMARY OF THE INVENTION

The invention provides a modular joint prosthesis in which one component, which is mountable within bone, is able to be offset with respect to another, attached component that is mountable upon the bone. Although the invention is applicable to a variety of joint prosthesis components, it is described herein for exemplary purposes with respect to a tibial component of a knee joint prothesis.

The joint prosthesis of the invention includes a tibial component having a superior mounting surface and an inferior bone contacting surface. The inferior bone contacting surface includes an elongate extension member with a proximal end and an open distal end. The prosthesis also includes a collar member and an elongate stem.

The collar member has a distal end and a proximal end which is matable with the distal end of the extension member. The collar member further has a bore extending therethrough from its proximal to its distal end. The elongate stem has proximal and distal ends, and the proximal end is matable with the distal end of the collar member. The elongate stem also has a cavity extending into its proximal end that is defined by inner side and distal walls.

The prosthesis further includes a bolt member having proximal and distal ends wherein a first longitudinal axis extending through the proximal end of the bolt member is substantially parallel to but offset from a second longitudinal axis extending through the distal end of the bolt member. The proximal end of the bolt member has a bolt head portion with at least one bolt head flat formed thereon effective to engage at least one flattened region formed in the distal end of the elongate extension member. The distal end of the bolt member extends beyond the distal end of the extension member and is matable within the cavity of the elongate stem such that the tibial component, collar member and elongate stem are secured to one another.

The collar and bolt member may be oriented such that offset is provided in either or both of the medial-lateral and anterior-posterior directions. This design enables the prosthesis of the invention to accommodate a variety of differing patient anatomies.

BRIEF DESCRIPTION OF THE DRAWINGS

FIG. 2 is a side sectional view from the medial-lateral direction of the joint prothesis components shown in FIG. 1 in an assembled condition.

FIG. 3 is a detailed view of portion A shown in FIG. 2.

DETAILED DESCRIPTION OF THE INVENTION

Figure 1:
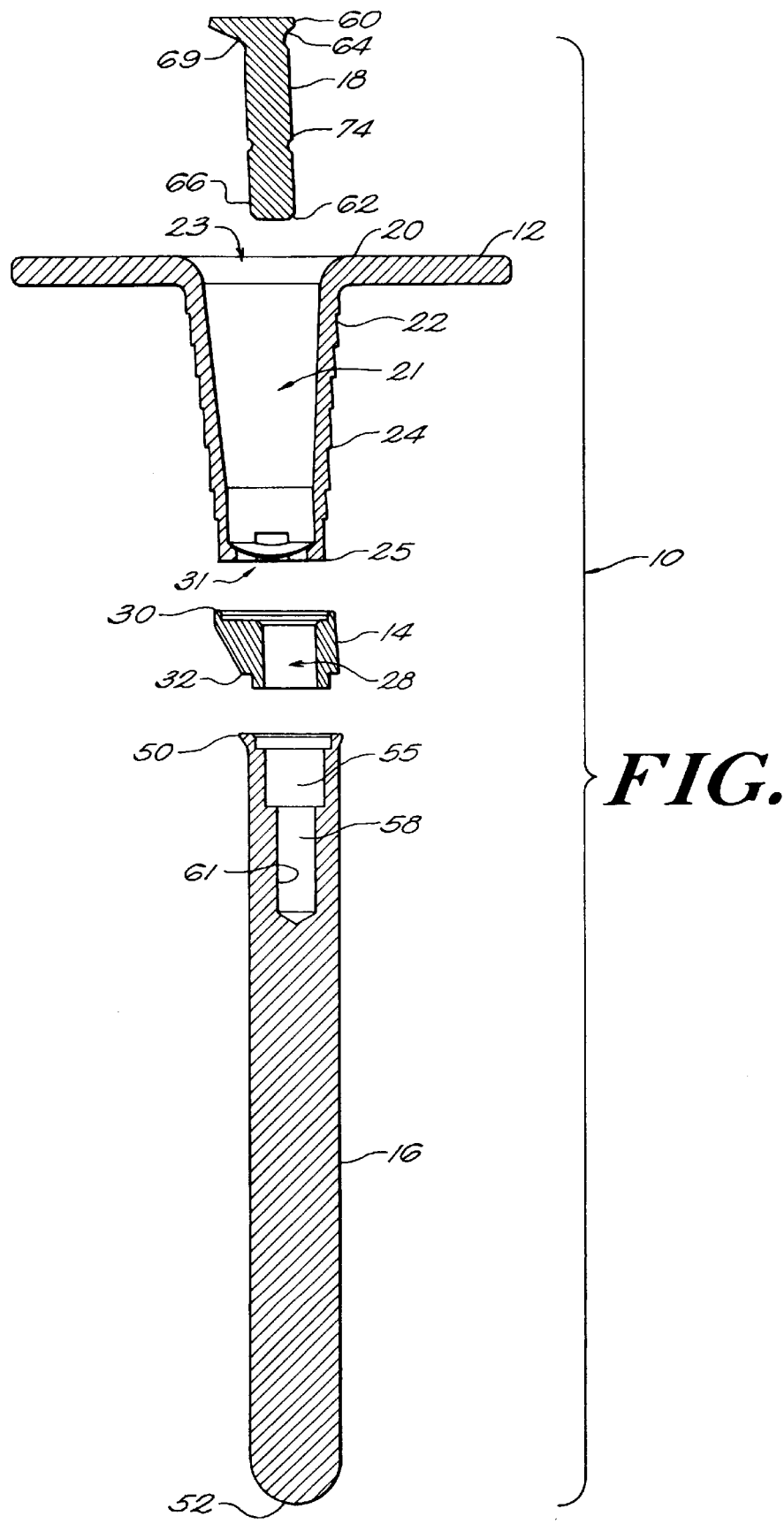
FIG. 1 is an exploded sectional view of a joint prosthesis of the present invention, including a tibial tray and a tibial stem that are matable together in an offset manner by a collar and bolt member.

Referring to FIG. 1, a joint prothesis component system 10 is provided. The component system 10 includes a tibial component, such as a tibial tray 12, a collar 14 and an elongate stem element 16 that are joined by a bolt member 18. In the embodiment illustrated herein, the joint prothesis components are shown as tibial trays and tibial stems useful as components of a knee joint prothesis system. It is understood, however, that the invention applies to components of other prothesis systems in which a longitudinal axis of a first element, that is mountable upon bone, is desired to be offset from the longitudinal axis of a second element that is attachable to the first element and mountable within bone.

With reference to FIGS. 1 and 2, the tibial tray element 12 can be a tibial tray of a type that is known in the art. The tibial tray 12 includes a superior surface 20 and an inferior surface 22, which is adapted to mount upon a patient's tibia (not shown). An elongate extension member 24 protrudes from the inferior surface 22 of the tibial tray 12. The elongate extension member 24 preferably is integral with the tibial tray and is intended to mount within the intramedullary canal of the tibia.

The tray 12 further has a bore 21 formed therethrough which extends from an opening 23 on the superior surface 20 of the tibial tray 12 to an opening 31 at a distal end 25 of the elongate extension 24. The opening 31 is shaped to accommodate bolt member 18 and in an exemplary embodiment, the opening may be elongated in either the medial-lateral direction or anterior-posterior direction.

Figure 4:
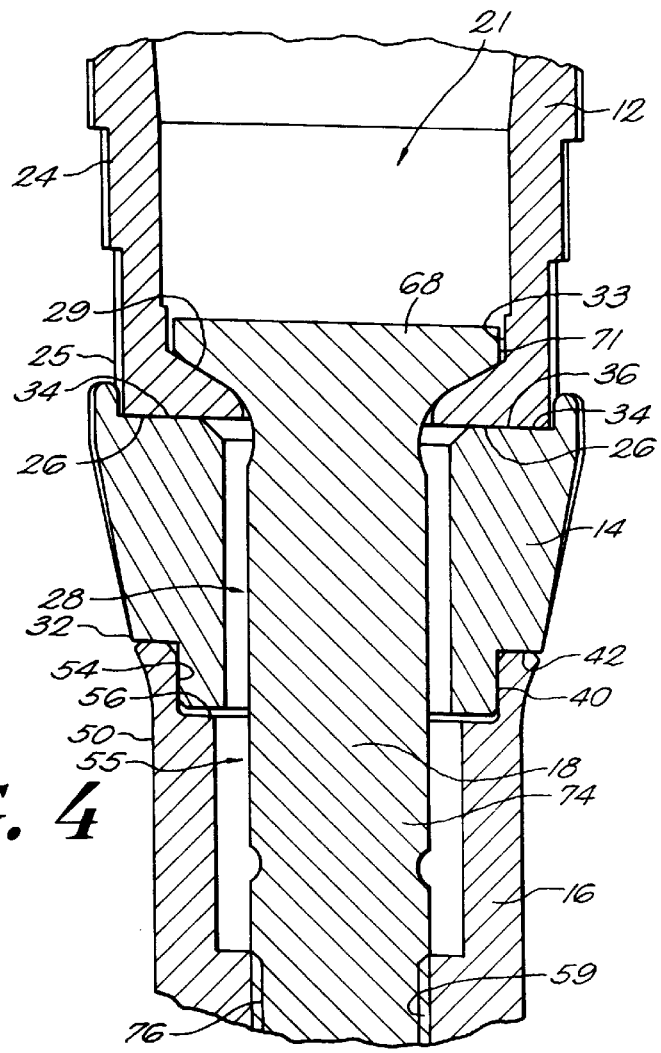
FIG. 4 is a detailed view of portion A shown in FIG. 2 from the anterior-posterior direction.
Figure 5:
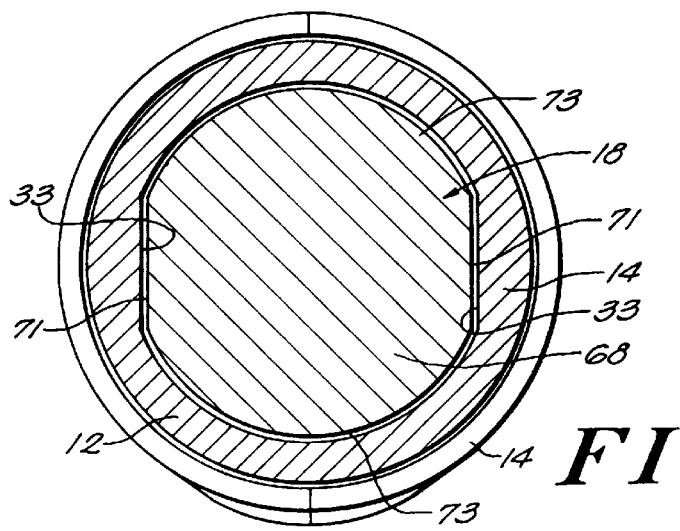
FIG. 5 is a sectional view through the bolt head shown in FIG. 4.

Referring to FIGS. 3 and 4, the distal end 25 of the elongate extension member 24 includes a connection surface 26 which extends partially or entirely about the circumference of the distal end 25. The connection surface 26 is mateable within collar 14 upon engagement of the distal end 25 of the elongate extension member 24 with collar 14. The distal end 25 of the elongate extension member 24 also includes a seating surface 29 internally disposed within bore 21, which is effective to seat bolt member 18 when the components of the prosthesis are assembled. As shown in FIGS. 4 and 5, the seating surface 29 includes at least one flattened sidewall portion 33 which is effective to engage corresponding bolt head flats 71 on bolt member 18. The flattened sidewall portion 33 prevents unwanted rotation of the bolt member 18 when the bolt member 18 is seated within the distal end 25 of elongate extension 24.

With reference to FIGS. 1, 3 and 4, the collar 14 includes an internal bore 28 which extends from a proximal end 30 to a distal end 32. The proximal end 30 of collar 14 includes a connection surface 34 which includes a proximally facing shoulder 36 which extends partially or entirely about the circumference of the proximal end 30. The connection surface 34 is effective to mate with and engage the complementary connection surface 26 formed on the distal end 25 of elongate extension 24. The distal end 32 of collar 14 also includes a connection surface 40 which includes a distally facing shoulder 42 which extends partially or entirely about the circumference of the distal end 32 of collar 14. The connection surface 40 is effective to mate with and engage a complementary connection surface 54 formed on a proximal end 50 of stem element 16.

The stem element 16, illustrated in FIGS. 1 and 2, preferably is of a type that is well known in the endoprothesis art. When secured to the remaining prosthesis components by bolt member 18, stem element 16 is intended to be mounted within the intramedullary canal of a patient's tibia in order to firmly secure the tibial component within the tibia. The stem element 16 is an elongate member having a proximal end 50 and a distal end 52. As shown in FIGS. 3 and 4, the proximal end 50 of the stem element 16 includes a connection surface 54, effective to mate with the distal end 32 of collar 14. The connection surface 54 includes a proximally facing shoulder 56, which is effective to engage complementary connection surface 40 formed on the distal end 32 of collar 14.

The proximal end 50 of the stem element 16 also has formed therein an opening 55 that leads to an internal cavity 58 which extends distally within the stem element 16. Cavity 58 preferably includes internal or female threads 59 on at least a portion of an inner surface 61 thereof. The threads 59 are effective to threadably engage corresponding male threads 74 formed on a distal end 62 of bolt member 18.

The use of a standard tibial stem that is able to threadingly mate with the distal end of a bolt element is desirable because it enables such tibial stems to be used with the tray and offset components of the present invention. Tibial stems are available with varying physical characteristics, including length, diameter and surface features. In essence this invention enables a surgeon to achieve a desired degree of offset, to accommodate virtually any anatomical peculiarity of a patient, while at the same time using a single, standard tibial stem. Although the illustrated tibial stem is intended to threadingly engage the bolt and collar member, it is understood that the tibial stem may alternatively be designed to engage the bolt and collar member through an interference fit or by mechanical interlock.

Referring to FIGS. 1–5, bolt member 18 is intended to join the tibial stem 16 to the tray element 12 such that these components are connected together in a desired orientation. The bolt member 18 includes a first, proximal end 60 and a second, distal end 62. The proximal and distal ends 60, 62, each have connection surfaces 64, 66, respectively, which allow the bolt member 18 to mate with the tray element 12 and the stem element 16 of the system 10. Further, as shown in FIG. 3, the proximal end 60 of the bolt member 18 has a longitudinal axis 70 extending therethrough that is offset from the longitudinal axis 72 extending through the distal end 62 of bolt member 18. The degree of offset can vary within the range of about 1 to 4 mm.

Referring to FIGS. 3–5, the bolt member 18 is designed such that the connection surface 64 includes a bolt head 68 having opposing bolt head flats 71 adjacent to opposing arcuate regions 73. Bolt head flats 71 are intended to engage corresponding flats 33 formed in the distal end 25 of elongate extension 34. The connection surface 64 further includes a distally facing, substantially spherical surface 69 which engages the seating surface 29 formed within the distal end 25 of elongate extension 24. Extending distally from the bolt head 68 is an elongate male member 74 which has male threads 76 formed at least partially thereon, and preferably over a distal portion of member 74. Threads 76 are adapted to threadably engage the female threads 59 formed within cavity 58 of stem element 16. It is understood that other connection schemes can be used as well. For example, appropriate tapering of the cavity 58 of the stem member 16 and the distal end 62 of bolt member 18 can effect an interference fit.

The mating engagement of the bolt head and distal end of the elongate extension 24 preferably positions and secures the bolt within the prosthesis. The position of the bolt head flats 71 relative to the flats 33 formed in the elongate extension 24 determines the orientation of the offset bolt within the prosthesis at an offset orientation in either direction of the medial-lateral plane. The engagement of flats 33 and bolt head flats 71 further prevent unwanted rotation of the bolt member when the components of the prosthesis are assembled.

FIGS. 1 and 3 illustrate a bolt member 18 that has a degree of lateral offset between longitudinal axes 70 and 72. Utilizing such offset bolt and collar components effects a corresponding offset between components of the prosthesis, such as shown in FIG. 2, where a longitudinal axis 80 of tibial component 12 is offset with respect to a longitudinal axis 82 of stem element 16. Because of the variable tibial anatomies encountered among knee arthroplasty patients more or less offset may be required. The lateral offset between axes 70 and 72, and consequently between axes 80 and 82, can vary depending upon a patient's anatomical requirements, but the offset generally is in the range of about 1 to 4 mm. A knee prosthesis system can include a variety of bolt members each having a different degree of lateral offset between axes 70 and 72, enabling a surgeon to utilize the adapter best suited to a given patient.

Another embodiment of the prosthesis system utilizing modular bolt and collar members is illustrated in FIGS. 6 through 10. While the embodiment shown and described above allows for offset in either direction of the medial-lateral plane, the embodiment shown in FIGS. 6 through 10 allows offset placement in the medial-lateral direction, the anterior-posterior direction, and virtually at any position between medial-lateral and anterior-posterior.

Figure 6:
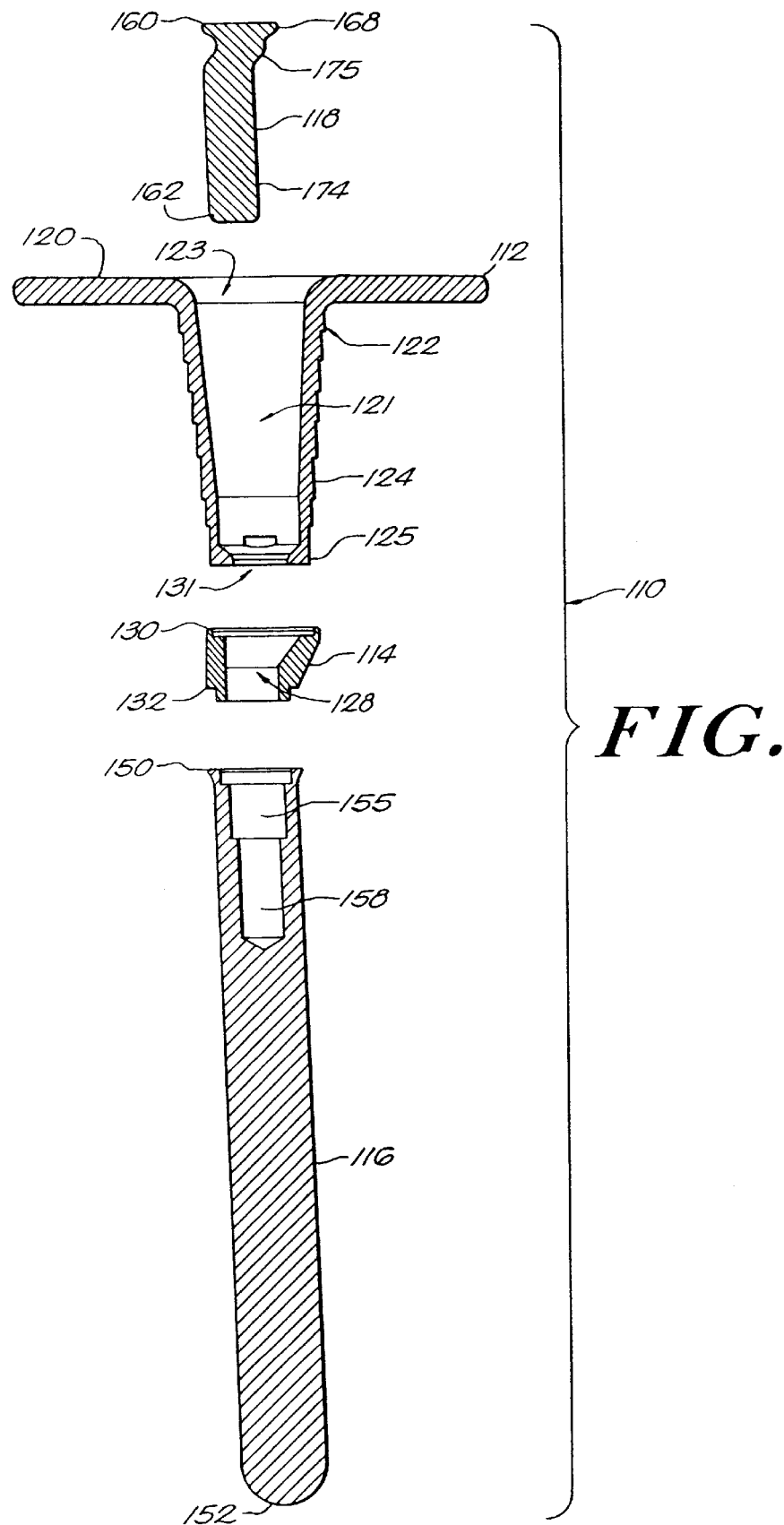
FIG. 6 is an exploded sectional view of another embodiment of the joint prosthesis of the present invention.
Figure 7:
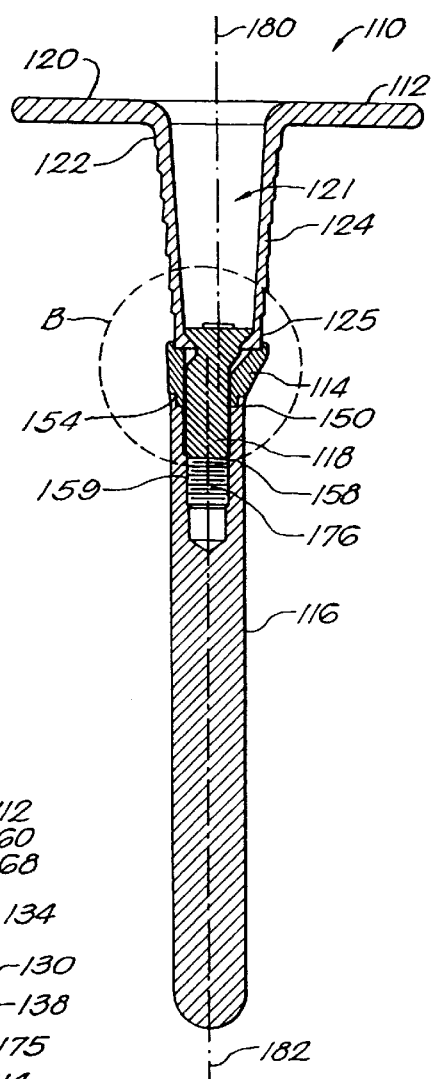
FIG. 7 is a side sectional view from the medial-lateral direction of the joint prothesis components shown in FIG. 6 in an assembled condition.

In this embodiment, illustrated in FIGS. 6 and 7, the system 110 includes a tibial tray 112, a collar 114 and an elongate stem element 116 that are joined by a bolt member 118. The tray 112 has a superior surface 120 and an inferior surface 122 with a longitudinal axis 180 extending there-through. An elongate extension 124 protrudes from the inferior surface 122 of the tibial tray 112 and is intended to mount within the intramedullary canal of the tibia.

Figure 8:
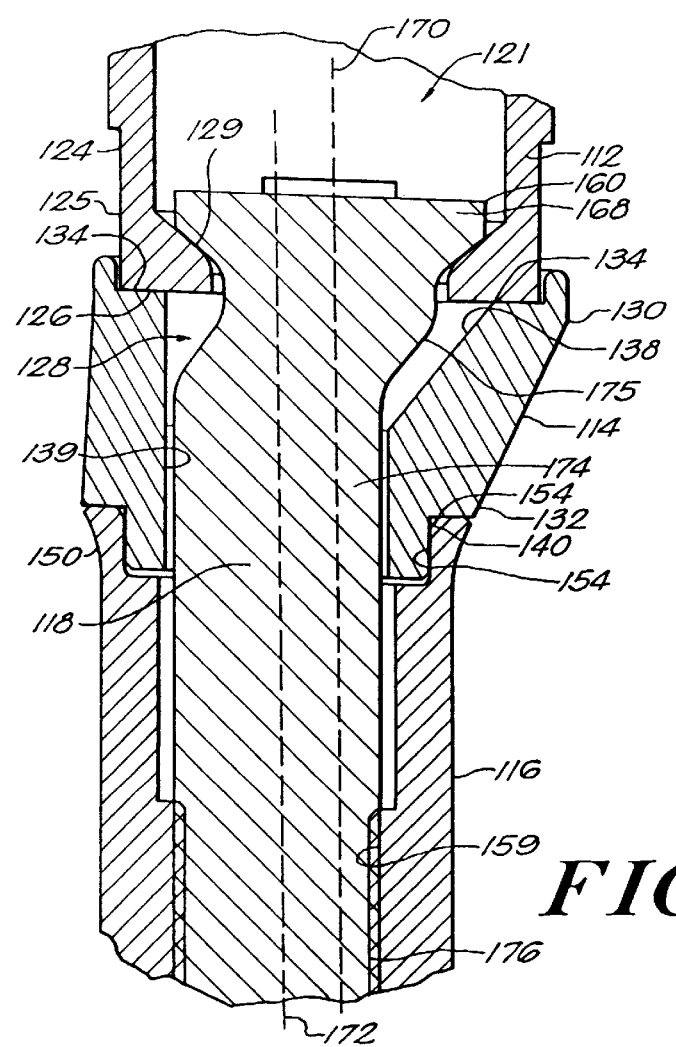
FIG. 8 is a detailed view of portion B shown in FIG. 7.
Figure 9:
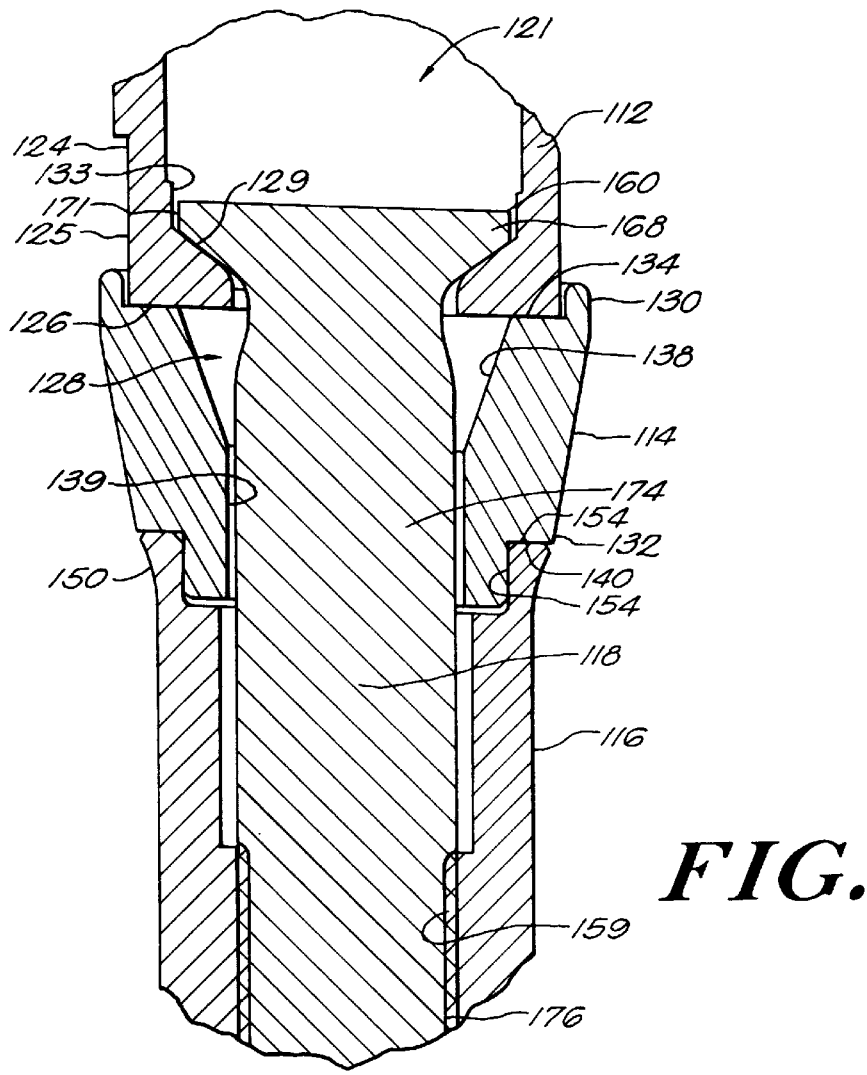
FIG. 9 is a detailed view of portion B shown in FIG. 7 from the anterior-posterior direction.
Figure 10:
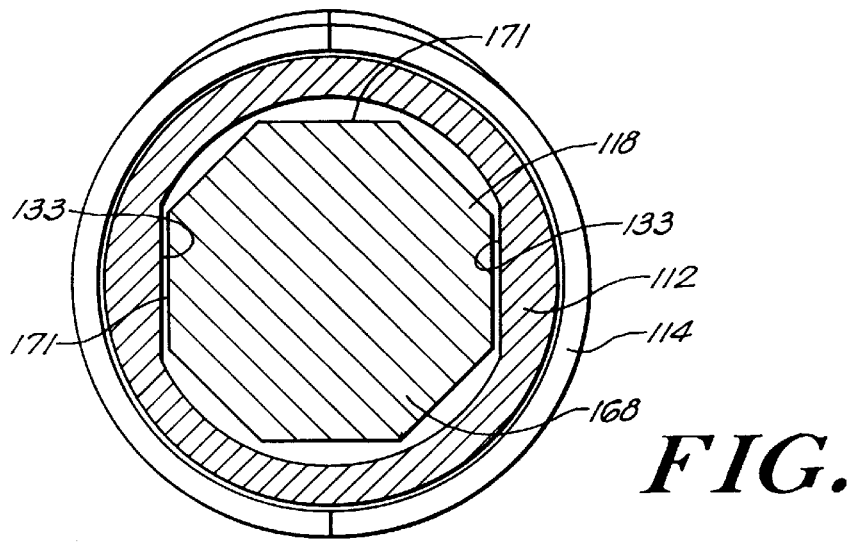
FIG. 10 is a sectional view through the bolt head shown in FIG. 9.

As shown in FIGS. 6 and 7, a bore 121 extends from opening 123 on the superior surface 120 of the tibial tray 112, through the elongate extension member 124 to an opening 131 at a distal end 125 of the elongate extension 124. The opening 131 at the distal end 125 of elongate extension member 124 may be substantially circular or any other shape suitable to accommodate bolt member 118. As shown in FIGS. 8 and 9, the distal end 125 of elongate extension 124 further includes a connection surface 126 which is mateable with a corresponding connection surface 134 formed on a proximal end 130 of collar 114. The distal end 125 of the elongate extension member 124 also includes a seating surface 129 internally disposed within bore 121. As shown in FIGS. 9 and 10, the seating surface 129 includes at least one flattened sidewall portion 133 which is effective to engage corresponding bolt head flats 171 formed on bolt member 118. The flattened sidewall portion 133 prevents unwanted rotation of the bolt member 118 when the bolt member 118 is seated within the distal end 125 of elongate extension 124.

As shown in FIGS. 8 and 9, collar 114 at a distal end 132 includes a connection surface 140 which is intended to engage a complementary connection surface 154 formed on a proximal end 150 of stem element 116. The collar 114 further includes an internal bore 128 which extends from the proximal end 130 to the distal end 132. The bore 128 is defined by inner sidewalls 138 and 139.

Referring to FIGS. 7 through 9, the collar 114 and bolt member 118 are configured to allow for offset of the tibial tray 112 with respect to the stem element 116. The collar 114 includes angled inner sidewalls 138 which are inclined to accommodate a similarly angled offset portion 175 of bolt member 118. In an exemplary embodiment, sidewall 138 is angled by an amount in the range of 15° to 60° with respect to adjacent sidewall portion 139.

Referring to FIGS. 6–10 the bolt member 118 further includes a head portion 168 and an elongate male member 174 extending distally from the head portion 168. The head portion 168 includes adjacent bolt head flats 171 effective to engage corresponding flats 133 formed internally in elongate extension 124. The engagement of flats 133 and bolt head flats 171 prevents unwanted rotation of the bolt member 118 when the components of the prosthesis are assembled together. Although the bolt head is shown with eight flats, any number of flats may be used to achieve offset placement of the prosthesis in the medial-lateral direction, the anterior-posterior direction, and virtually any position between medial-lateral and anterior-posterior.

Male member 174 also has male threads 176 formed at least partially thereon and preferably, over a distal portion of member 174. The bolt member 118 is constructed such that a longitudinal axis 170 extending through a first, proximal end 160 thereof is offset from a longitudinal axis 172 extending through a second, distal end 162 thereof by an amount in the range of about 1 to 4 mm. As so configured, the bolt element 118 may be mounted to the other components such that the longitudinal axis 180 of tray element 112 is offset from a longitudinal axis 182 of stem element 116 in either or both the medial-lateral direction, the anterior-posterior direction, or at virtually any orientation between medial-lateral and anterior-posterior.

As shown in FIG. 7, one way in which the components can be joined together is through a threaded connection between the bolt member 118 and the stem element 116. Once assembled, distal end 162 of bolt member 118 extends beyond the distal end 125 of the elongate extension 124 of the tibial tray 112 when the bolt member 118 is properly seated in the elongate extension 124. The threaded distal end 162 of bolt 118 is passed through collar 114 to engage corresponding threads 159 formed in a bolt cavity 158 within the stem element 116. In this configuration, the components are secured together and can be selectively assembled and de-assembled simply by accessing the bolt head through the tibial element 112.

One of ordinary skill in the art will appreciate that the joint prosthesis is system described herein can be used with a variety of joint prosthesis, including knee joint prostheses. The system is particularly useful with a rotatable knee joint prosthesis in which a tibial bearing element (not shown) is mounted upon the superior surface 20, 120 of tibial tray 12, 112 or such that it is able to rotate and/or translate relative to the tibial tray.

It is understood that various modifications can be made to the present invention without departing from the intended scope thereof. The entirety of all references noted herein is expressly incorporated by reference herein.

What is claimed is:

1. A joint prosthesis, comprising:
   a tibial component having a superior mounting surface and an inferior bone contacting surface, the inferior bone contacting surface including a substantially conical elongate extension member having a bore extending therethrough from the inferior surface to an opening formed in a distal end of the elongate extension member, the distal end having at least one flattened region formed therein;

a collar member having a distal end, and a proximal end that is matable with the distal end of the extension member, the collar member further having a bore extending therethrough from the proximal to the distal ends;

an elongate stem having a distal end and a proximal end that is matable with the distal end of the collar member, the stem further having a cavity formed into the proximal end that is defined by inner side and distal walls; and a bolt member having proximal and distal ends oriented such that a first longitudinal axis extending centrally through the proximal end is substantially parallel to but offset from a second longitudinal axis extending centrally through the distal end, the proximal end having a bolt head portion having at least one bolt head flat effective to engage the at least one flattened region within the distal end of the extension member and the distal end being matable within the cavity of the elongate stem such that the tibial component, collar member and elongate stem are secured to one another.

2. The joint prosthesis of claim 1, wherein the first longitudinal axis is colinear with a central longitudinal axis of the tibial component.

3. The joint prosthesis of claim 2, wherein the second longitudinal axis is colinear with a central longitudinal axis of the elongate stem.

4. The joint prosthesis of claim 1, wherein the tibial component is a tibial tray and the elongate stem is a tibial stem.

5. The joint prosthesis of claim 1, wherein the elongate stem cavity has internal threads.

6. The joint prosthesis of claim 5, wherein the distal end of the bolt member is threaded to threadably mate within the elongate stem cavity.

7. The joint prosthesis of claim 1, wherein the first and second longitudinal axes are offset from each other by approximately 1 to 4 mm.

8. The joint prosthesis of claim 1, wherein the bolt member is offset in at least one of an anterior-posterior and medial-lateral directions with respect to a tibia.

9. The joint prosthesis of claim 1, wherein the opening in the distal end of the elongate extension member is elongated in the medial-lateral direction.

10. The joint prosthesis of claim 1, wherein the opening in the distal end of the elongate extension member is substantially circular.

11. A joint prosthesis system, comprising:

a tibial tray having a superior mounting surface and an inferior bone contacting surface and a substantially conical elongate extension member with proximal and distal ends;

at least one collar, each of the at least one collars having proximal and distal ends with a bore extending therethrough, wherein the proximal end is matable with the distal end of the extension member;

at least one elongate stem having proximal and distal ends with a cavity extending into the proximal end, the proximal end being matable with the distal end of the at least one collar; and at least one bolt member having proximal and distal ends oriented such that a first longitudinal axis extending centrally through the proximal end is substantially parallel to but offset from a second longitudinal axis extending centrally through the distal end, the proximal end being a head portion with at least one tray engaging flat formed thereon that is matable within the distal end of the extension member and the distal end of the at least one bolt member being matable within the cavity of the stem to secure the tibial tray, the collar and the elongate stem to one another such that a longitudinal axis of the elongate stem is parallel to but offset with respect to a central axis of the tibial tray.

* * * * *